United States Patent [19] [11] 4,318,746
Claffey et al. [45] Mar. 9, 1982

[54] HIGHLY STABLE GEL, ITS USE AND MANUFACTURE

[75] Inventors: Kevin Claffey, Brooklyn; Lloyd Osipow, New York, both of N.Y.

[73] Assignee: IPCO Corporation, White Plains, N.Y.

[21] Appl. No.: 110,450

[22] Filed: Jan. 8, 1980

[51] Int. Cl.³ .......................... C08L 1/28; C08L 5/00
[52] U.S. Cl. .................................... 106/194; 106/171; 106/189; 106/197 R; 106/197 C; 106/206; 106/208; 106/209
[58] Field of Search .................. 106/205–209, 106/197 R, 197 C, 194; 252/316

[56] References Cited

U.S. PATENT DOCUMENTS

| | | | |
|---|---|---|---|
| 2,886,564 | 5/1959 | Holvsz | 260/239.5 |
| 2,927,055 | 1/1960 | Lanzet | 252/316 |
| 3,027,333 | 3/1962 | Friedman | 251/521 |
| 3,567,657 | 3/1971 | Lichtenstein | 252/500 |
| 3,607,788 | 9/1971 | Adolph et al. | 252/510 |
| 3,710,782 | 1/1973 | Hauser | 128/696 |
| 3,862,094 | 1/1975 | Shinohara et al. | 528/362 |
| 3,901,218 | 8/1975 | Buchalter | 128/641 |
| 3,956,173 | 11/1976 | Towle | 252/316 |
| 3,961,623 | 6/1976 | Milani et al. | 128/639 |
| 3,989,035 | 11/1976 | Zuehlsdorff | 128/641 |
| 3,989,050 | 11/1976 | Buchalter | 128/419 R |
| 3,998,215 | 2/1976 | Anderson et al. | 128/641 |
| 4,027,664 | 6/1977 | Heavner, Jr. et al. | 123/198 E |
| 4,066,078 | 1/1978 | Berg | 128/641 |
| 4,096,327 | 6/1978 | Guiseley | 106/205 |
| 4,109,648 | 8/1978 | Larke et al. | 128/639 |
| 4,125,110 | 11/1978 | Hymes | 128/641 |

Primary Examiner—Allan Lieberman
Attorney, Agent, or Firm—Pennie & Edmonds

[57] ABSTRACT

An improved gel comprises a first polymer that dissolves, disperses or hydrates in hot water and forms or can be made to form a rigid gel on cooling, a second polymer that is insoluble in hot water and that dissolves or hydrates on cooling and is compatible with said hot water soluble polymer, and water. The gel is made by combining the first polymer and water, heating the resulting solution enough that the first polymer dissolves or hydrates, adding the hot water insoluble polymer, and then cooling.

36 Claims, No Drawings

HIGHLY STABLE GEL, ITS USE AND MANUFACTURE

CROSS REFERENCE TO RELATED APPLICATIONS

Related applications filed concurrently herewith, are "Disposable Electrode and Its Method of Manufacture", and "Stable Gel Electrode," both of which are assigned to the assignee of the present application and are incorporated herein by reference.

BACKGROUND AND SUMMARY OF THE INVENTION

This concerns a gel which combines many desirable properties with ease of manufacture. The gel is firm, cohesive and adhesive. It is stable at relatively high temperatures (80 degrees C.) as well as low temperatures (below 0 degrees C.); and it is a good electrical conductor. As a result, the gel makes a superior medical electrode. Because of its stability and low irritation potential, the gel may also be used for topical administration of drugs. Another application is in an improved room freshener.

The gel comprises:

a first polymer that dissolves, hydrates or disperses in hot water and that forms or can be made to form a rigid gel on cooling, a hot water insoluble polymer that dissolves or hydrates on cooling and is compatible with said first polymer, and water, said polymers having been combined in hot water.

For convenience, a polymer that dissolves, hydrates or disperses in hot water will be referred to herein as a hot water soluble polymer.

Preferably the hot water soluble polymer is kappa carrageenan; and the hot water insoluble polymer is hydroxypropylmethylcellulose (HPMC). Advantageously, the kappa carreennan and HPMC are food grade products and the gel also contains common preservatives such as benzyl alcohol, methyl paraben, and propyl paraben. In some applications, it is desirable to use an electrolyte such as potassium chloride or potassium carbonate in this gel to increase its rigidity or conductivity. However, carrageenan itself is a relatively good conductor and the gel may be used as an electrode gel without the addition of a separate electrolyte.

If desired, glycerol, propylene glycol or other polyhydric alcohols may be used to reduce the rate of evaporation from the gel; and Locust bean gum, sodium carboxymethylcellulose, other compatible gums, sodium stearate, potassium stearate or other compatible soaps may be used to plasticize it. Surfactants such as the sodium linear alkylate sulfonates (e.g., Ultrawet DS) and the sodium linear alkylbenzene sulfonates (e.g., Sulframine 85) may be used with this gel to increase its adhesion.

Because a hot water soluble polymer is combined in hot water with a hot water insoluble polymer, a high proportion of the hot water insoluble polymer can be incorporated into the hot water soluble polymer at elevated temperatures without causing a prohibitive increase in the viscosity of the hot composition. Consequently, the gel can be manufactured rapidly in large quantities using only simple heating and stirring equipment.

BEST MODE OF CARRYING OUT THE INVENTION

In general, the gel of the present invention comprises:

a first polymer that dissolves, hydrates or disperses in hot water and that forms or can be made to form a rigid gel on cooling;

a hot water insoluble polymer that dissolves or hydrates on cooling and is compatible with said first polymer; and water, said polymers having been combined in hot water.

A preferred embodiment of the gel of the present invention comprises the following:

| Materials | Weight % |
| --- | --- |
| Genugel LC-4 | 2.00 |
| Methocel E4M, 4000 cps. | 6.00 |
| Benzyl alcohol, N.F. | 0.60 |
| Methyl paraben | 0.15 |
| Propyl paraben | 0.05 |
| Potassium Chloride (or Potassium Carbonate) | 0.50 |
| Water | 90.70 |

Genugel LC-4 is a food grade calcium kappa carrageenan which contains a small quantity of locust bean gum, sucrose and potassium phosphate. It is available from Hercules, Inc., Paramus, N.J. Carrageenan forms a sol in hot water and a rigid, cohesive gel upon cooling. Methocel, E4M, 4000 cps., is a food grade hydroxypropylmethylcellulose (HPMC) with a viscosity range of about 4,000 cps. It is available from Dow Chemical, Midland, Mich. Methocel E4M, 4000 cps., is a hot water insoluble polymer which becomes soluble on cooling to form an adhesive sol. It functions as an adhesive agent and a stabilizer in this embodiment. HPMC has reversible thermal gelation properties in water. At sufficient concentrations, it begins to hydrate to form a viscous, sticky sol when cooled to less than about 60 degrees C. When warmed to above about 55 to 60 degrees C. it becomes a gel and it becomes insoluble at approximately 65 degrees C. These properties make it possible to incorporate relatively large quantities of HPMC into a hot carrageenan dispersion without excessive increase in viscosity such as would prohibit the use of conventional heating and stirring equipment in the manufacture of this gel.

Benzyl alcohol, methyl paraben and propyl paraben are common preservatives. In addition, the relatively large amount of benzyl alcohol used appears to increase the adhesion of the gel. Potassium chloride (or potassium carbonate) serves as an electrolyte and also increases the rigidity of the carrageenan gel. In some applications the use of potassium carbonate may be preferred over potassium chloride since chloride ions may be a source of topical irritation.

The preferred embodiment has several advantages: it is firm and cohesive, it has good adhesion, it is a good electrical conductor and it is stable at both high and low temperatures. In addition, the gel's properties are attained in a composition that is mostly water and uses relatively low quantities of gelant in contrast to other electrically-conductive cohesive or rigid gels, which require substantially more gelant in order to be firm and cohesive. Moreover, because the adhesive agent becomes active as the geling agent becomes insoluble, cohesion and adhesion develop in the gel at the same time and the gel will adhere to skin without the need to wet the skin or the gel with water.

Experiments with the gel have indicated that it will retain its cohesion, adhesion and conductivity without any significant loss after storage at high temperatures (about 80 degrees C.) or cycling through freeze-thaw cycles. High temperature stability is believed to be caused by the use of both a hot water soluble polymer and a hot water insoluble polymer. It is further improved by the use of potassium chloride. HPMC becomes more gelatinous with increasing temperature, thereby increasing the structural integrity of the gel, up to about 65 degrees C. when it precipitates. Carrageenan gels are reversible so that they will liquefy again when they are reheated. However, they must be heated to a significantly higher temperature to break down the gel structure than was required initially to form the gel. Thus, while the initial gel temperature of the preferred embodiment is about 60-70 degrees C. the cooled gel must be reheated to about 85-95 degrees C. before it will liquefy again. Potassium chloride reacts selectively with kappa or iota carrageenan to form the more insoluble potassium salt, thereby increasing the gel temperature of the composition and providing a stronger gel structure on cooling. The higher gel temperature contributes to the thermal stability of the gel and makes it possible to manufacture the preferred embodiment using conventional processing equipment. The stability of the preferred embodiment in freeze-thaw cycling probably results from the increase in solubility of HPMC as the temperature decreases. This limits or prevents syneresis during freeze-thaw cycling.

The preferred embodiment may advantageously be modified by the addition of humectants, such as glycerol, propylene glycol and other polyhydric alcohols and plasticizers, such as Locust bean gum, sodium carboxymethylcellulose, other compatible gums, sodium or potassium stearate and other compatible soaps. Glycerol, at 4% to 10% by weight of the composition, helps to reduce the rate of evaporation from the exposed surface of the electrode. Potassium stearate, at 0.5% to 1% by weight of the composition, plasticizes the gel so that it will more readily conform to the surface to which it is applied. Obviously the plasticizer should be compatible with the hot water soluble and hot water insoluble polymers. The concentration of the plasticizer should be such that it is sufficiently soluble to act as a plasticizer at ambient temperatures, and it should make minimal contribution to the viscosity of the composition. Generally, the plasticizer can be used at a concentration of about 0.5% to about 50% of the weight of the hot water soluble polymer. Surfactants such as the sodium linear alkylate sulfonates (e.g. Ultrawet DS) and the sodium linear alkylbenzene sulfonates (e.g. Sulframine 85) may also be used to increase the adhesion of this gel.

The gel of the present invention has the advantage that it is relatively rigid and adhesive at temperatures below 60 to 65 degrees C. but will flow readily at elevated temperatures. A preferred method for making the gel is as follows. As cool water is stirred in a mixing vessel, potassium chloride is added followed by a powdered hot water soluble polymer, preferably Genugel LC-4. While stirring rapidly, the resulting dispersion is heated slowly to a temperature which is hot enough to dissolve or hydrate the hot water soluble polymer and is greater than that at which the hot water insoluble polymer begins to dehydrate. For the preferred embodiment the dispersion is heated to about 85 degrees C. where it is stirred for about 20 minutes. At approximately 65 degrees C., the viscosity of the Genugel dispersion begins to increase rapidly as the Genugel begins to hydrate. It will then begin to thin out again at 75 degrees C.

After stirring the hydrated gel, a powdered hot water insoluble polymer is added slowly by sifting. Preferably the hot water insoluble polymer is Methocel E4M, 4000 cps., powder, which has a temperature of dehydration of about 65 degrees C. After stirring for 20 minutes more, the preservatives such as benzyl alcohol and methyl and propyl parabens are added. After all the ingredients have been added, the composition should be stirred until it looks smooth and uniform, at which point the composition is ready to be poured into molds or sheets which define the end product. For example, the gel can be poured into holes 50 in the foam rings of FIG. 3 of the concurrently filed patent application entitled "Stable, Gel Electrode and Its Method of Manufacture," assigned to the assignee of the present application. During the pouring operation the temperature of the composition should be maintained above the gel temperature; and after pouring, the composition should be allowed to cool and become rigid. For the preferred embodiment the temperature of the composition is maintained at about 85 degrees C. during pouring and a rigid gel is formed upon cooling to about 60-65 degrees C.

It is preferable to add the hot water soluble polymer after the potassium chloride because this appears to delay the onset of hydration and/or slow its rate. For example, in the case of Genugel, hydration appears to be delayed until the temperature is raised to about 65 degrees C. This has the advantage of keeping the dispersion relatively thin and helps to prevent lumping. The stirring operations should be carried out at all times in such a way as to avoid entrapping air. Large amounts of air may provide oxygen for microbes, increase syneresis or reduce the adhesive character of the gel. Care should also be taken to avoid rapid heating or excessive temperatures which can cause the hot water soluble polymer to dehydrate and cake on the walls of the mixing vessel. A suitable mixer for use in practicing the invention is the Lightning Mixer.

The particular formula for the gel set forth above is preferred. Numerous alternatives are available for the constituents of the gel and they may be used in concentrations which vary substantially from those set forth in the preferred formula. In general, the hot water soluble polymer may be selected from the class of polymers known as natural gums or from chemically modified or semi-synthetic derivatives of the natural gums. The hot water soluble polymer may also be one which can be made to gel on cooling by the addition of specific cations or anions. While kappa and iota carrageenans at sufficient concentration form rigid cohesive gels when cooled, at lower concentrations it is necessary to add small quantities of potassium cations to the carrageenans in order to form a rigid gel. In addition, small quantities of potassium cations when added to carrageenan will form a gel that is even more rigid and cohesive than is formed in their absence. Examples of various polymers which are hot water soluble and gel on cooling include the carrageenans, Irish Moss, and Agar. Examples of hot water soluble polymers that can be made to gel on cooling include Guar, Tragacanth and the alginates. Advantageously the hot water soluble polymer that forms a gel on cooling should be reversible when heated in order to promote stability at high temperatures.

Generally, the concentration of the hot water soluble polymer ranges from about 0.5% to about 5.0% by weight of the composition with better results at concentrations of about 1.5 to 3% by weight. This concentration is considerably lower than that typically required in other electrically-conductive gels which are cohesive and rigid. The lower limit of concentration is defined by the point at which it is impossible to form a cohesive gel. This limit can be lowered by increasing the concentration of other geling agents that may be present in the composition. For example, a mixture of about 2.0% by weight of kappa carrageenan and 1.0% by weight of potassium chloride will produce a gel with approximately the same gel strength as a composition containing about 3.0% to 4.0% by weight kappa carrageenan and no potassium chloride. The upper limit of concentration cannot be precisely determined. It is reached when the polymeric solution becomes too viscous to stir. This point varies with the particular polymer and is determined, to considerable degree, by the skill of the operator in mixing, stirring and heating the polymer. As will be apparent, the particular temperature at which the hot water soluble polymer dissolves, hydrates or disperses in water will vary with the polymer.

The hot water insoluble polymer which becomes soluble on cooling and forms an adhesive sol may be selected from the class of non-ionic polymers that exhibit reversible thermal gelation properties in water. Examples of such polymers include cellulose derivatives such as methyl cellulose, hydroxypropyl cellulose, hydroxypropyl methylcellulose and hydroxybutyl methylcellulose. These cellulose derivatives are all available from Dow Chemical as different types of Methocels. In general the concentration of the hot water insoluble polymer ranges from about 2.0% to about 20.0% by weight of the composition with the optimum concentration varying with the viscosity of the polymer. For example, the 4,000 cps. grades of HPMC have been found to give optimum adhesion at concentrations of about 6% by weight of the composition and acceptable performance between about 5 and 7.5% composition weight. Lower concentrations give poor adhesion because there is not enough of the polymer in the composition while higher concentrations give poor adhesion because they reduce the wetness of the surface of the gel. It is estimated that hot water insoluble polymers with viscosities up to 500 cps. may be used in concentrations on the order of 20% by weight of the composition and that polymers with viscosities in excess of 4,000 cps. may be used in concentrations on the order of about 2% by weight. The particular temperature of the dispersion to which the hot water insoluble polymer is added can vary with the polymer. In general, such dispersion should be at a temperature greater than the temperature of dehydration of the hot water insoluble polymer.

Of course, any hot water insoluble polymer that is used must be compatible with the hot water soluble polymer so that the gel retains its desired properties during normal use. When Genugel LC-4 is used as the hot water soluble polymer, it has been found that all of the cellulose derivatives identified above are compatible.

Carrageenan is a polyelectrolyte and the preferred embodiment is electrically-conductive even without the addition of a separate electrolyte. If, however, the hot water soluble polymer is not sufficiently conductive, a small quantity of electrolyte such as sodium chloride, potassium chloride, potassium carbonate, or potassium gluconate may be added to the composition. To minimize the chance of topical irritation caused by the chloride ions, potassium carbonate or potassium gluconate are preferred. Generally the concentration of the electrolyte is about 0.2% to 2.0% by weight of the composition. Of course, the electrolyte should be chosen so that it does not seriously impair the cohesion, adhesion and stability of the gel formed by the hot water soluble polymer and the hot water insoluble polymer.

As noted above, potassium chloride also functions as a geling agent with kappa and iota carrageenan. Because of the sulphate ester content of kappa and iota carrageenan, they react specifically with potassium cations to form a firmer gel on cooling. The weight of the potassium chloride used to provide a firmer gel should range from about 5 to 50% of the weight of the carrageenan.

Surprisingly, it has also been found that a much more adhesive gel is formed if potassium chloride or potassium carbonate is not used in the electrode gel. While such a gel is not as rigid or as conductive as one with a small quantity of potassium chloride or potassium carbonate, it is well adapted for use in the type of electrodes employed in transcutaneous electrical nerve stimulation and EKG equipment.

A preferred embodiment of said gel is:

|  | Weight % |
|---|---|
| Genugel LC-4 | 2.00 |
| Methocel F4M, premium | 6.00 |
| Benzyl alcohol | 0.10 |
| Methyl paraben | 0.15 |
| Propyl paraben | 0.05 |
| Water | 91.70 |

As suggested above, in the absence of any potassium chloride the gel temperature of this alternative is lower, being about 40 to 45 degrees C. The process for manufacturing this gel is substantially the same as that for manufacturing the preferred embodiment except, of course, that no potassium chloride is used. As in the case of the other gel formulations discussed above, variations in concentration and substitutions may be made within the spirit and scope of the invention.

There are many possible applications for the highly stable gel of the present invention. As is apparent from the patent applications cross-referenced above, the gel can be used in an electrode and is especially useful in a stable, disposable electrode for patient monitoring or stimulation. As is known in the medical arts, numerous electrical signals generated by the body may be monitored by means of an electrode attached to the skin and connected to suitable electronic equipment. See, for example, U.S. Pat. Nos. 4,066,078; 4,109,648 and 4,125,110. As is also set forth in these patents and U.S. Pat. No. 3,961,623, electrodes are also used in patient stimulation apparatus such as defibrillators and pain killers. Regardless of the purpose, such electrodes must provide good signal transmission between the patient's skin and the leads to the electronic equipment. Moreover, the electrodes used for stimulation purposes must provide such signal transmission without creating "hot spots" which may burn the patient. To permit use as a disposable electrode, the electrode must also be simple and easy to use and inexpensive to manufacture and distribute. As detailed in the above-referenced applications, the gel of the present invention has been found to provide a superior disposable electrode for monitoring and stimulation.

As for other applications, the gel of the present invention is an unusually stable vehicle having numerous cosmetic and pharmaceutical applications. For example, it may be used as a dosage form for the percutaneous administration or topical application of various drugs or antibiotics. It may be used as an occlusive dressing or a burn ointment. As long as they are compatible, oils, oil soluble ingredients, and other water-insoluble materials may be incorporated into the gel before it is cooled by emulsifying or dispersing them into the hot dispersion. Since the preferred embodiment is edible, it may serve as a palatable vehicle for the ingestion of drugs or as a bulking-type of laxative. Because it is rigid and stable the gel may also be used as the vehicle for a solid room freshening agent. From the foregoing discussion numerous other uses will be apparent to those skilled in the art.

Numerous other variations in the compositions and methods described above will be apparent to those skilled in the art.

What is claimed is:

1. A gel comprising:
    a first polymer in weight percentage of at least 0.5 percent that dissolves, disperses or hydrates in hot water and that forms or can be made to form a rigid gel on cooling,
    a second polymer in weight percentage of at least 2.0 percent that is insoluble in hot water and that dissolves or hydrates on cooling and is compatible with said first polymer, and
    water, said polymers having been combined in hot water.

2. The gel of claim 1 wherein said first polymer is carrageenan and said second polymer is a cellulose derivative.

3. The gel of claim 1 wherein said first polymer is carrageenan in weight percentage of about 2% and said second polymer is hydroxypropylmethylcellulose having a viscosity of about 4000 cps., in weight percentage of about 5% to 7.5%.

4. The gel of claim 3 further comprising potassium chloride or potassium carbonate in weight percentage of approximately 0.5%.

5. The gel of any one of claims 1, 2 and 3 further comprising an electrolyte.

6. A gel comprising:
    water,
    a first polymer in weight percentage of at least 0.5 percent that has been dissolved, dispersed or hydrated in said water and that forms or can be made to form a rigid gel upon cooling, and
    a second polymer in weight percentage of at least 2.0 percent that is insoluble in hot water, that dissolves or hydrates on cooling, that is compatible with said first polymer and that has been combined with said first polymer and water at a temperature greater than that at which it begins to dehydrate.

7. the gel of claim 6 wherein said first polymer is carrageenan and said second polymer is a cellulose derivative.

8. The gel of claim 6 or claim 7 further comprising an electrolyte.

9. A gel comprising:
    water,
    a first polymer in weight percentage of at least 0.5 percent that has been dissolved, dispersed or hydrated in said water and that forms or can be made to form a rigid gel upon cooling, and
    a second polymer in weight percentage of at least 2.0 percent that is insoluble in hot water, that dissolves or hydrates on cooling, that is compatible with said first polymer and that has been combined with said first polymer and water when said first polymer is dissolved, dispersed or hydrated in said water.

10. The gel of claim 9 wherein said first polymer is carrageenan and said second polymer is a cellulose derivative.

11. The gel of claim 9 or claim 10 further comprising an electrolyte.

12. A gel comprising water in weight percentage of at least 50%, carrageenan in weight percentage of about 0.5 to 5.0% and a non-ionic cellulose derivative that is compatible with carrageenan, insoluble in hot water and that dissolves or hydrates on cooling in weight percentage of about 2% to 20%.

13. The gel of claim 12 wherein the carrageenan is in weight percentage of about 2% and the cellulose derivative has a viscosity of about 4,000 cps and is in weight percentage of about 5% to 7.5%.

14. The gel of claim 12 or claim 13 further comprising potassium chloride or potassium carbonate in weight percentage of approximately 5 to 50% of the weight of the carrageenan.

15. The gel of claim 12 or 13 further comprising an electrolyte.

16. A method of forming a gel comprising the steps of:
    combining a first polymer and water, said first polymer being one that dissolves, disperses or hydrates in hot water,
    raising the temperature of said water and polymer enough that said polymer dissolves, disperses or hydrates,
    adding a hot water insoluble polymer to said water and first polymer when they are at a temperature higher than that at which said first polymer dissolves, disperses or hydrates and higher than that at which said hot water insoluble polymer begins to dehydrate and
    cooling the resulting composition to form a rigid gel.

17. The method of claim 16 wherein said first polymer is carrageenan, said hot water insoluble polymer is a non-ionic cellulose derivative compatible with carrageenan, and the solution of water and carrageenan is heated to about 85 degrees C.

18. The method of claim 17 wherein the cellulose derivative has a viscosity of about 4000 cps., the weight percentage of carrageenan in the rigid gel is about 2% and the weight percentage of the cellulose derivative in the rigid gel is about 5 to 7.5%.

19. The method of claim 18 wherein the cellulose derivative is hydroxypropylmethylcellulose.

20. The method of any one of claims 16, 17, 18, and 19 wherein the first polymer and water are combined by adding the polymer to water while stirring and the composition formed by adding the hot water insoluble polymer to said solution is stirred until it is smooth and uniform before it is cooled.

21. The method of any one of claims 16, 17, 18 and 19 further comprising the step of adding an electrolyte to the water before it is combined with said first polymer.

22. The method of any one of claims 16, 17, 18 and 19 further comprising the step of forming an emulsion or disperson by adding a non-water-soluble ingredient to said composition before it is cooled to form a rigid gel.

23. A method of forming a gel comprising the steps of:
dissolving, dispersing or hydrating a first polymer in water, said first polymer being one that forms or can be made to form a rigid gel on cooling,
adding a hot water insoluble polymer to said first polymer and water when said first polymer is dissolved, dispersed or hydrated in said water, said second polymer being one that dissolves or hydrates on cooling, and
cooling the resulting composition to form a rigid gel.

24. The method of claim 23 wherein said first polymer is carrageenan, said hot water insoluble polymer is a non-ionic cellulose derivative compatible with carrageenan, and the water and carrageenan are heated to about 85 degrees C. before the cellulose derivative is added.

25. The method of claim 23 or claim 24 wherein the first polymer and water are combined by adding the polymer to water while stirring and the composition formed by adding the hot water insoluble polymer to said first polymer and water is stirred until it is smooth and uniform before it is cooled.

26. The method of claim 23 or claim 24 further comprising the step of adding an electrolyte to the water before it is combined with said first polymer.

27. The method of of claim 23 further comprising the step of forming an emulsion or disperson by adding a non-water-soluble ingredient to said composition before it is cooled to form a rigid gel.

28. A method of forming a gel comprising the steps of:
dissolving, dispersing or hydrating a first polymer in water, said first polymer being one that forms or can be made to form a rigid gel on cooling,
adding a hot water insoluble polymer to said first polymer and water when they are at a temperature higher than that at which said hot water insoluble polymer begins to dehydrate, and
cooling the resulting composition to form a rigid gel.

29. The method of claim 28 wherein said first polymer is carrageenan, said hot water insoluble polymer is a non-ionic cellulose derivative compatible with carrageenan, and the water and carrageenan are heated to about 85 degrees C. before the cellulose derivative is added.

30. The method of of claim 28 or claim 29 wherein the first polymer and water are combined by adding the polymer to water while stirring and the composition formed by adding the hot water insoluble polymer to said first polymer and water is stirred until it is smooth and uniform before it is cooled.

31. The method of claim 28 or claim 29 further comprising the step of adding an electrolyte to the water before it is combined with said first polymer.

32. The method of of claim 28 further comprising the step of forming an emulsion or dispersion by adding a non-water-soluble ingredient to said composition before it is cooled to form a rigid gel.

33. A gel comprising water in weight percentage in at least 50%, carrageenan in weight percentage of about 0.5 to 5.0% and hydroxypropylmethylcellulose in weight percentage of about 2% to 20%.

34. The gel of claim 33 wherein the carrageenan is in weight percentage of about 2% and the hydroxypropylmethylcellulose has a viscosity of about 4,000 cps and is in weight percentage of about 5% to 7.5%.

* * * * *